(12) United States Patent
Martin et al.

(10) Patent No.: US 8,840,681 B2
(45) Date of Patent: Sep. 23, 2014

(54) BREATHABLE MICROFRAME PROSTHETIC INTERFACE

(75) Inventors: Jay Martin, Oklahoma City, OK (US); Paul J. Biermann, Columbia, MD (US)

(73) Assignee: The Johns Hopkins University, Baltimore, MD (US)

(*) Notice: Subject to any disclaimer, the term of this patent is extended or adjusted under 35 U.S.C. 154(b) by 146 days.

(21) Appl. No.: 13/523,481

(22) Filed: Jun. 14, 2012

(65) Prior Publication Data

US 2013/0024009 A1    Jan. 24, 2013

Related U.S. Application Data

(60) Provisional application No. 61/497,639, filed on Jun. 16, 2011.

(51) Int. Cl.
*A61F 2/78* (2006.01)
*A61F 2/58* (2006.01)
*A61F 2/72* (2006.01)

(52) U.S. Cl.
CPC . *A61F 2/72* (2013.01); *A61F 2/581* (2013.01); *A61F 2/78* (2013.01)
USPC .............................................. 623/57; 623/58

(58) Field of Classification Search
CPC ............. A61F 2/50; A61F 2/58; A61F 2/581; A61F 2/582; A61F 2/54; A61F 2/546; A61F 2/78; A61F 2002/5016; A61F 2002/503; A61F 2002/7862; A61F 2002/7881
USPC ............................................ 623/57, 58, 66.1

See application file for complete search history.

(56) References Cited

U.S. PATENT DOCUMENTS

| | | | |
|---|---|---|---|
| 1,272,179 A | 7/1918 | Anderson et al. | |
| 1,299,505 A * | 4/1919 | Petron | 623/59 |
| 1,323,671 A | 12/1919 | Baehr | |
| 1,466,163 A * | 8/1923 | Harris | 623/58 |
| 1,479,297 A | 1/1924 | Harris | |
| 2,033,150 A | 3/1936 | Radtke | |
| 2,537,402 A * | 1/1951 | Fitch | 623/57 |
| 2,686,319 A | 8/1954 | Alderson | |
| 4,790,855 A | 12/1988 | Jolly | |
| 6,652,596 B2 * | 11/2003 | Smith et al. | 623/32 |

FOREIGN PATENT DOCUMENTS

GB    151372    9/1920
GB    198539    6/1923

* cited by examiner

*Primary Examiner* — Randy Shay
(74) *Attorney, Agent, or Firm* — Noah J. Hayward

(57) ABSTRACT

A prosthetic interface includes an orientation assembly, a mounting plate and a load bearing assembly. The orientation assembly includes an anterior frame portion and a posterior frame portion. The anterior frame portion extends over an anterior portion of a torso of a wearer of the prosthetic interface. The posterior frame portion extends over a posterior portion of the torso. The mounting plate is disposed at an intersection of the posterior frame portion and the anterior frame portion. The mounting plate forms a structure to which a prosthetic limb is attachable. The load bearing assembly includes breathable fabric forming a load distribution matrix to distribute a load on the mounting plate over portions of the torso with which the fabric is in contact.

16 Claims, 5 Drawing Sheets

BREATHABLE MICROFRAME PROSTHETIC INTERFACE

CROSS-REFERENCE TO RELATED APPLICATIONS

This application claims priority to and the benefit of copending U.S. Provisional Application No. 61/497,639, filed on Jun. 16, 2011, the entire contents of which are hereby incorporated herein by reference.

STATEMENT OF GOVERNMENTAL INTEREST

This invention was made with U.S. Government support under contract number N66001-06-C-8005 awarded by the Defense Advanced Research Projects Agency (DARPA). The Government has certain rights in the invention.

TECHNICAL FIELD

Example embodiments generally relate to prosthetic devices and, more particularly, relate to a microframe prosthetic interface that employs breathable materials.

BACKGROUND

Prosthetic devices have continued to evolve over time to improve the functional capabilities and aesthetic appearance of such devices. However, such improvements typically require increased weight and structural rigidity. This renders the resultant prosthetic devices relatively uncomfortable to wear.

One type of prosthetic device that produces particular challenges in this regard is a shoulder disarticulation level prosthetic socket. Traditional sockets that are commonly employed for such prosthetic devices include substantially full frame and rigid sockets that cover the residual limb and, in some cases, portions of the torso a well, with rigid, non-breathable plastic or laminated resin. Such a device retains heat and moisture close to the wearer's body. Additionally, such a device creates pressure points when certain load conditions are encountered. Thus, both sweating and discomfort are encountered when the conventional prosthetic socket is worn.

BRIEF SUMMARY OF SOME EXAMPLES

Accordingly, some example embodiments may enable the provision of a relatively light structure for supporting a prosthetic interface. In this regard, some example embodiments may employ a relatively small microframe, which may be supported by a breathable fabric that extends around a portion of the torso. Accordingly, for example, the breathable fabric may form a load distribution fabric matrix that anchors the prosthetic interface to the body without the creation of local areas that trap heat or bear high loads, thereby increasing the comfort of the wearer.

In one example embodiment, a prosthetic interface is provided. The prosthetic interface may include an orientation assembly, a mounting plate and a load bearing assembly. The orientation assembly may include an anterior frame portion and a posterior frame portion. The anterior frame portion may be configured to extend over an anterior portion of a torso of a wearer of the prosthetic interface. The posterior frame portion may be configured to extend over a posterior portion of the torso. The mounting plate may be disposed at an intersection of the posterior frame portion and the anterior frame portion. The mounting plate may form a structure to which a prosthetic limb is attachable. The load bearing assembly may include breathable fabric forming a load distribution matrix to distribute a load on the mounting plate over portions of the torso with which the fabric is in contact.

BRIEF DESCRIPTION OF THE SEVERAL VIEWS OF THE DRAWING(S)

Having thus described example embodiments of the invention in general terms, reference will now be made to the accompanying drawings, which are not necessarily drawn to scale, and wherein:

DETAILED DESCRIPTION

Figure 1:
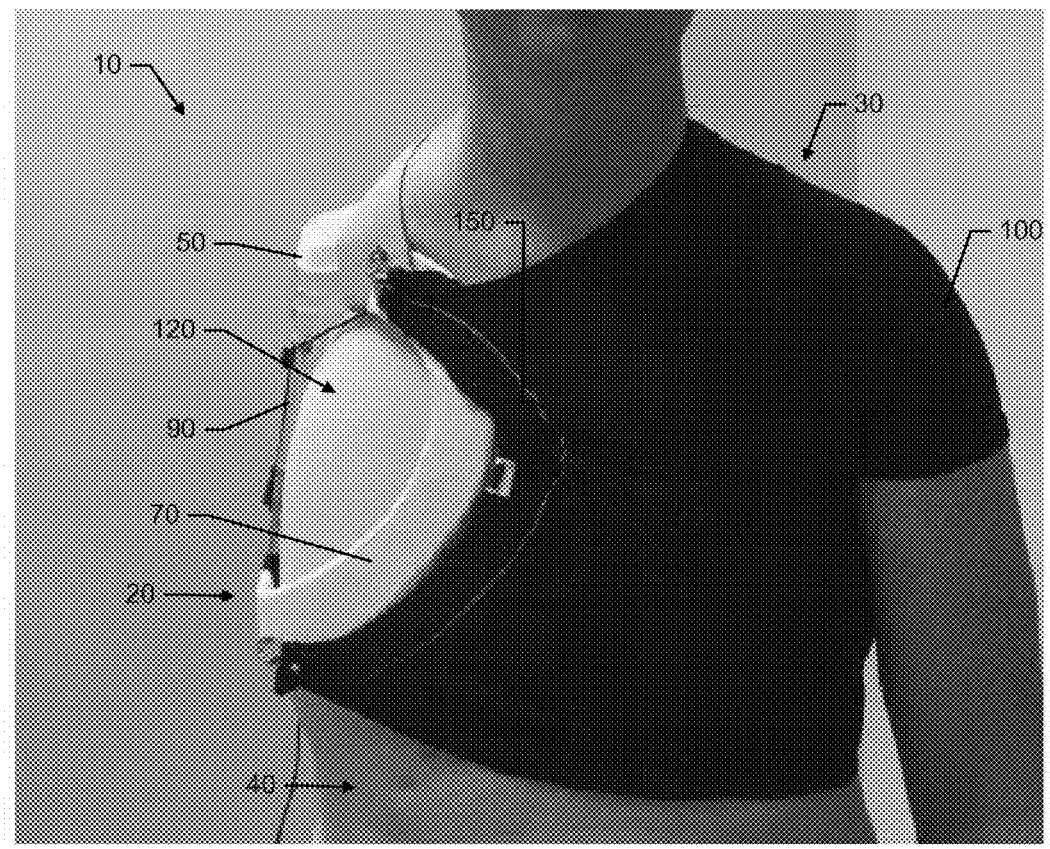
FIG. 1 is a front view of a prosthetic interface according to an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

Some example embodiments may enable a relatively light structure for supporting a prosthetic interface (e.g., socket system) to be provided. Such a structure may employ a relatively small microframe that facilitates distribution of limb forces across more of the torso than just the local areas that contact the microframe. This distribution may be accomplished via a breathable fabric that extends around a portion of the torso. Accordingly, the trapping of heat and localization of pressure points that is commonly encountered in connection with laminated, resin based socket systems may be avoided and the comfort of the wearer may be enhanced.

An example embodiment will be described herein as it relates to a shoulder prosthetic interface. However, it should be appreciated that some example embodiments may alternatively be practiced in connection with other prosthetic devices.

FIG. 1 is a front view of a prosthetic interface 10 according to an example embodiment. As shown in FIG. 1, the prosthetic interface 10 may include two main portions including an orientation assembly and a load bearing assembly. The orientation assembly may be embodied as a frame portion 20, while the load bearing assembly may be embodied as a fabric portion 30. The frame portion 20 may provide for proper orientation of the fabric portion 30 with respect to a torso 40 of the wearer of the prosthetic interface 10 so that loads may be distributed through the fabric portion 30 to minimize the incidence of pressure points that may reduce the comfort level of the wearer.

The frame portion 20 may include a mounting plate 50 to which a prosthetic arm (e.g., see prosthetic arm 60 of FIG. 4) may be attached. As such, the frame portion 20 may be configured to be disposed proximate to the missing or residual limb and the fabric portion 30 may be attached to the frame portion 20 and also wrap around a portion of the torso 40 of the wearer of the prosthetic interface 10. The fabric portion 30 may be configured to form a load distribution fabric matrix to distribute forces due to loading associated with the prosthetic interface 10 (e.g., forces on the prosthetic arm 60) so that the forces are not merely transmitted to the body of the wearer at a limited number of pressure points, but are instead distributed over the torso 40 more evenly, and through the material of the fabric portion 30. A downward oriented load on the mounting plate 50 may therefore be distributed substantially perpendicularly with respect to the orientation of the exerted force away from the frame portion 20 via the fabric portion. Moreover, as will be discussed in greater detail below, the load may be distributed away from the frame portion 20 three hundred and sixty degrees around the torso 40.

Figure 2:
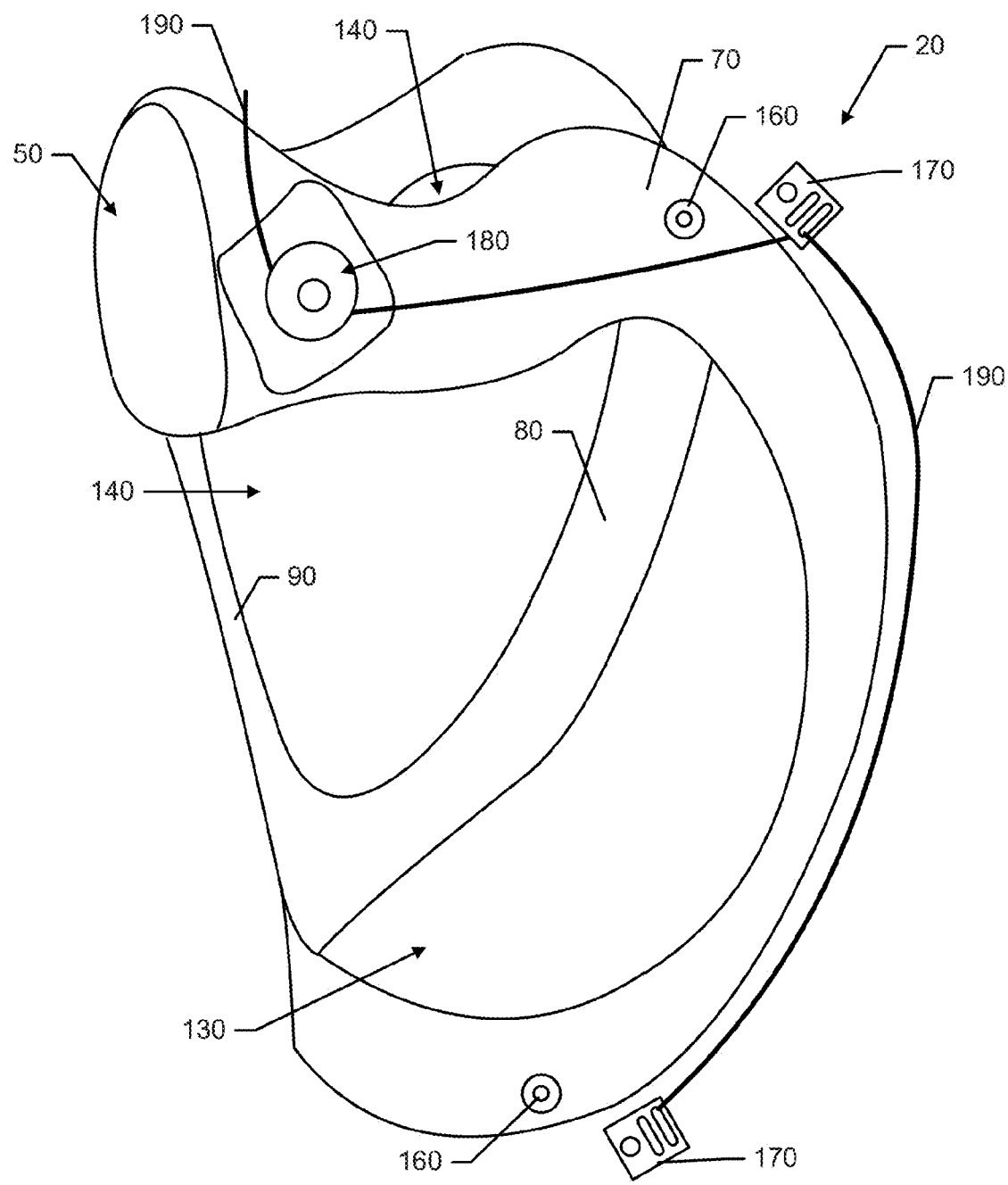
FIG. 2 shows a more detailed view of a frame portion of the prosthetic interface as seen from an anterior or front perspective and with a fabric portion of the prosthetic interface removed according to an example embodiment.

FIG. 2 shows a more detailed view of the frame portion 20 as seen from an anterior or front perspective and with the fabric portion 30 removed. The frame portion 20 generally extends over an anterior and posterior of the torso 40 and extends inward toward the midline of the torso 40. As can be seen from FIG. 2, the frame portion 20 includes an anterior frame member 70 and a posterior frame member 80 that meet at one end thereof at the mounting plate 50, approximately at the location from which the missing arm would otherwise extend. The anterior frame member 70 and the posterior frame member 80 may meet at the opposite end thereof at a location beneath where the armpit of the wearer would be and proximate to the latissimus dorsi muscles and ribs of the wearer.

Both the anterior frame member 70 and the posterior frame member 80 may extend away from where they meet and toward the midline of the wearer on both the front and back sides of the torso 40, respectively. The anterior frame member 70 and the posterior frame member 80 may each be substantially flat plates of material bent to have an arcuate shape such that an interior flat face of each of the anterior frame member 70 and the posterior frame member 80 are configured to conform to the body contours of the wearer. In some embodiments, the anterior frame member 70 and the posterior frame member 80 may be formed based on a mold of the wearer in order to custom fit the anterior frame member 70 and the posterior frame member 80 to the wearer. Thus, for example, the mold of the wearer may be used as a basis for molding, casting or otherwise forming the frame portion 20 from a unitary piece of material. Alternatively, the anterior frame member 70 and the posterior frame member 80 may be formed to one or more predefined shapes and/or sizes. Thus, for example, a number of sizes and/or shapes that are common for different age, gender, limb status, or categories based on other characteristics may be generated.

The material used to form the frame portion 20 may be a resin, light metal, plastic or other similar material. In an example embodiment, the material may be rigid, but flexible. Rubber coating, padding or other materials may employed on surfaces of the frame portion 20 to increase the comfort of the wearer and prevent direct contact between the material of the frame portion 20 and the skin of the wearer.

In an example embodiment, each of the anterior frame member 70 and the posterior frame member 80 may generally have a "C-shape". The arcuate portions of the respective C-shaped members may extend away from each other such that the portions of the anterior frame member 70 and the posterior frame member 80 that correspond to the straight portions of the C-shape are adjacent to each other while remaining portions of the respective C-shapes extend outward. However, the anterior frame member 70 and the posterior frame member 80 may also be bent such that they conform to the contours of the body. As such, when viewed from above, the frame portion 20 may form a "U-shape". In an example embodiment, a proximal or top portion of the posterior frame member 80 that extends away from the mounting plate 50 may be disposed proximate to the superspinatus groove of the wearer when worn. Meanwhile, the substantially mirrored portion of the anterior frame member 70 may be disposed proximate to the deltopectoral groove below the clavicle of the wearer when worn.

Figure 3:
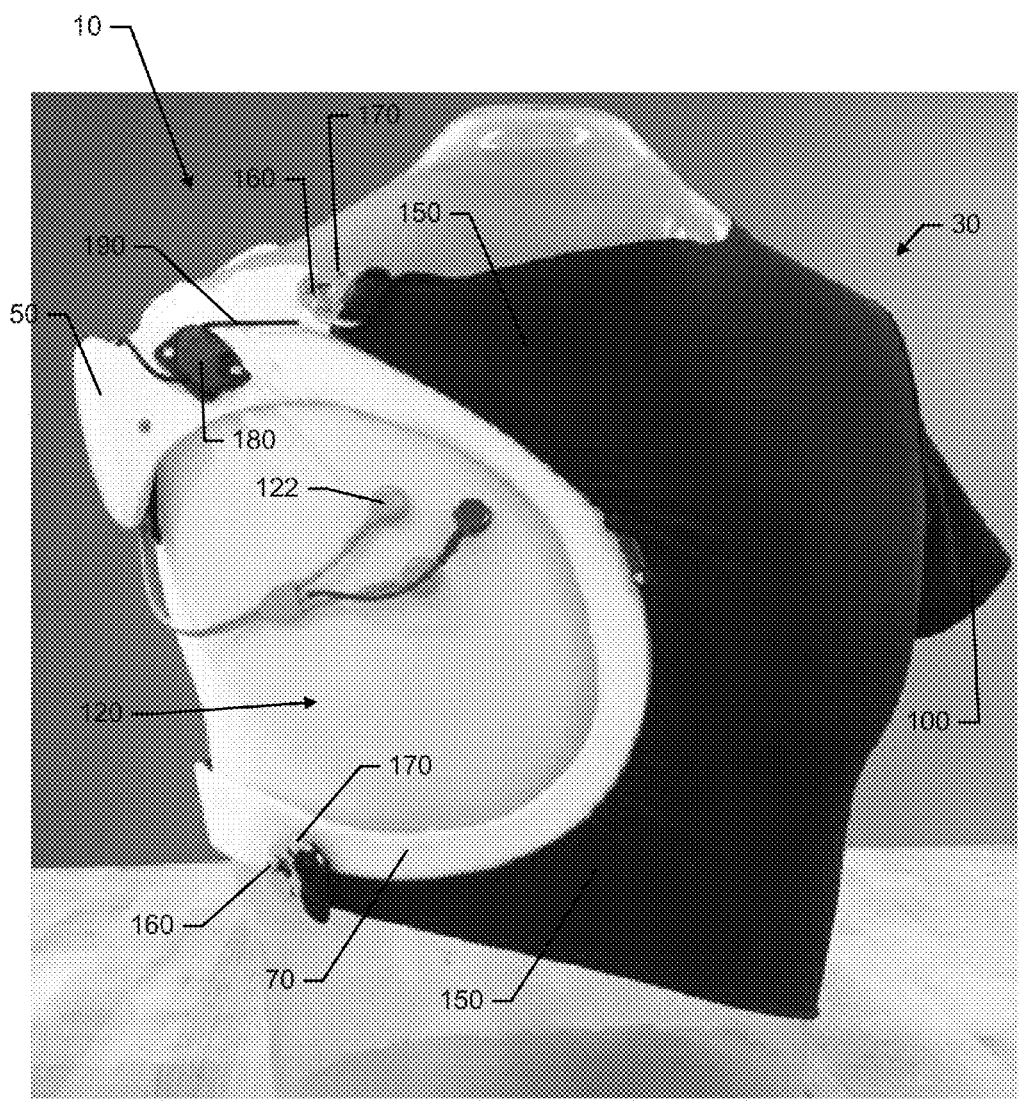
FIG. 3 illustrates a perspective view of the prosthetic interface according to another example embodiment.

In some embodiments, a strut 90 may be provided for structural support at the intersection between the anterior frame member 70 and the posterior frame member 80. In other words, the strut 90 may extend between the points of intersection of the distal ends of the C-shaped arcuate portions. Although the strut 90 may be employed in some embodiments, it should be appreciated that the strut 90 need not be included in all embodiments (such as is the case in the embodiment of FIG. 1). When included, the strut 90 may be provided to add structural support to prevent deformation of the frame portion 20 responsive to forces that would otherwise tend to compress the anterior frame member 70 and the posterior frame member 80 vertically. Of note, however, the strut 90 is not necessary in all cases because the frame portion 20 is generally not required as a load bearing member. Instead, the frame portion 20 generally functions to hold the fabric portion 30 in a desirable orientation. Thus, the fabric portion 30 generally bears a vast majority of the load (e.g., greater than 90%), while the frame portion 20 (and the strut 90, if employed) instead provide advantageous positioning surfaces to which the fabric portion 30 can be attached to create a load distribution matrix that distributes the load over the torso 40 (and particularly over the opposite side of the torso 40) via the many fibers of the fabric portion that extend around the torso 40. As such, the fabric portion 30 forms a plurality of "straps" that are held in a matrix (i.e., the matrix of the fabric or material used for the fabric portion 30) to distribute the load on the prosthetic interface 10. FIG. 3 illustrates a perspective view of the prosthetic interface 10 according to another example embodiment. In the example of FIG. 3, the strut 90 of FIGS. 1 and 2 is removed.

In an example embodiment, the fabric portion 30 may be made of a material that is relatively light and breathable. The material may be flexible and stretchable while further enabling moisture to be wicked away from the body of the wearer. In some embodiments, a woven graphite cloth material may be used for the fabric portion 30. Some example embodiments may employ 10%/90% elastane fabric in the fabric portion 30.

The fabric portion 30 may be formed to approximate the shape of a typical T-shirt with one arm portion removed. As such, in some embodiments, the fabric portion 30 may include at least some fabric extending from the anterior frame member 70 to the posterior frame member 80 via the opposite shoulder region (e.g., the region between the neck of the wearer and either the sleeve 100 or the opposite arm) and/or at least some fabric extending from the anterior frame member 70 to the posterior frame member 80 via the portion of the torso 40 that is between the shoulder and waist of the wearer. Thus, in some embodiments, the fabric portion 30 may extend from the anterior frame member 70 to the posterior frame member 80 via the opposite side of the wearers torso (i.e., the side opposite with respect to the prosthetic interface 10).

Figure 4:
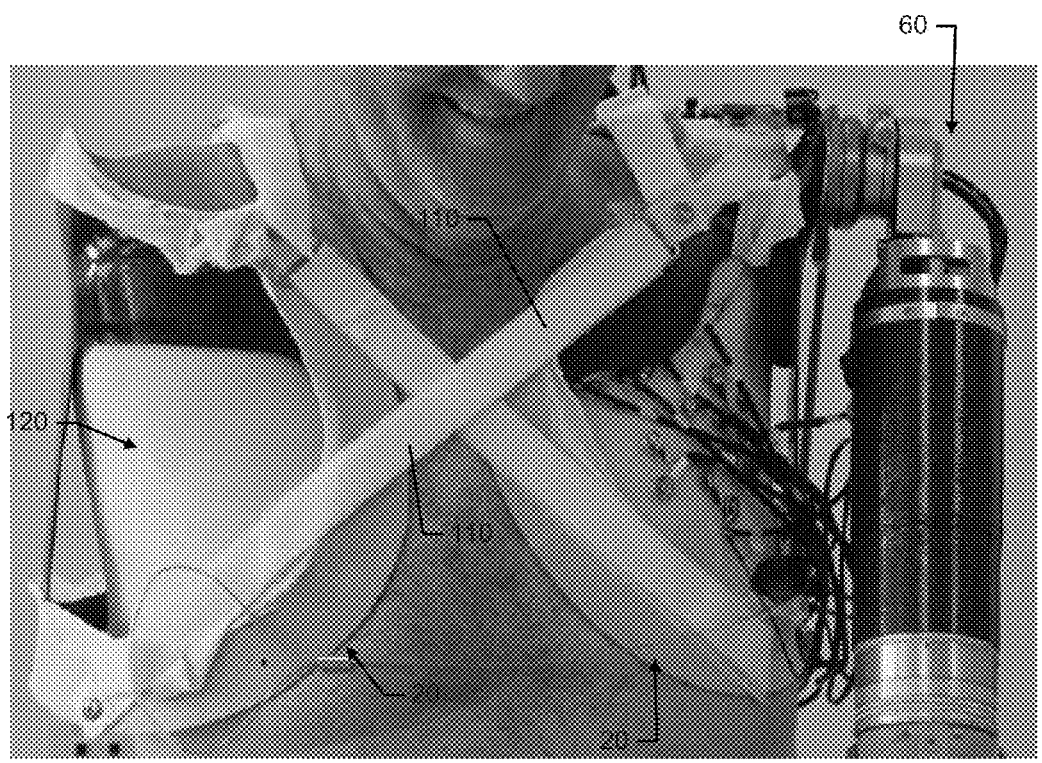
FIG. 4 illustrates a front view of two prosthetic interfaces coupled together according to an example embodiment.

Although the fabric portion 30 of FIGS. 1 and 3 is shown to include a sleeve 100 for the limb opposite the missing limb, it is not necessary that the sleeve 100 be included. Moreover, in some cases, two frame portions 20 may be employed for double amputees, or others who are missing both arms at the shoulder. FIG. 4 illustrates an example of such an arrangement. In this example, the fabric portion is embodied as one or more discrete straps 110 that connect from a bottom portion of one anterior frame member 70 to a top portion of the opposing anterior frame member. Similarly, the fabric portion may be embodied as discrete straps that connect a bottom portion of one posterior frame member 80 to a top portion of the opposing posterior frame member.

In some embodiments, the fabric portion 30 may further include a drum portion 120 that may be disposed substantially proximate to an anterior frame gap 130 formed in the space defined by the anterior frame member 70 and substantially proximate to a posterior frame gap 140 formed in a space defined by the posterior frame member 80. The drum portion 120 may therefore be stretched over an interior portion of the frame portion 20 (i.e., the side of the frame portion 20 that is proximate to the wearer's skin). In some embodiments, the drum portion 120 may be affixed to the frame portion 20 via a hook and loop fastener. In this regard, it should be noted that the hook portion of the fastener may be disposed on an internal and/or external surface of the frame portion 20 and the drum portion 120 may include or be embodied as the loop portion of the fastener. However, other fixing methods could alternatively be employed (e.g., adhesive or distributed fixed points of attachment). In any case, some embodiments may wrap the drum portion around an external periphery of the frame portion 20 so that the frame portion 20 itself does not contact the skin of the wearer, and so that a relatively secure fit may be achieved.

The drum portion 120 may further facilitate distribution of loads encountered by the prosthetic interface 10 and reduce loading on the frame portion 20. In this regard, for example, the drum portion 120 may be affixed to the frame portion 20 such that it is stretched between the anterior frame member 70 and the posterior frame member 80 so that the fabric of the drum portion 120 may be further stretched when the prosthetic interface 10 is donned. The stretching of the drum portion 120 may further assist in load distribution to reduce the amount of load borne by the distal lateral portion of the frame portion 20 (e.g., where the anterior frame member 70 and the posterior frame member 80 meet. Accordingly, when a load is encountered at the mounting plate 50 in a downward direction, rather than merely deforming the frame portion 20 downward or imparting a force on the distal lateral portion of the frame portion 20, the drum portion 120 may distribute the load over the entire part of the body with which the drum portion 120 is in contact. This arrangement may provide for a 360 degree distribution of load around the torso 40 of the wearer instead of concentrating load bearing responsibility in more discrete locations since the fabric portion 30 may extend 360 degrees around the torso 40.

The drum portion 120 of some embodiments may further be utilized for providing a mechanism by which to position electrodes 122 proximate to the wearer's skin. The electrodes 122 may snap onto the drum portion 120 and be held in contact with the wearer's skin (and muscles located proximate to the contact point) so that electrical signals may be generated for control of the prosthetic arm responsive to movement of muscles that the electrodes contact. Any number of electrodes 122 may be employed in various embodiments. Moreover, other types of electrodes may also be employed.

The fabric proximate to the missing arm portion may be connected to the frame portion 20 to enable the fabric portion 30 to carry and distribute loads encountered by the prosthetic interface 10 over the fabric portion. More specifically, the fabric portion 30 may have an anterior interface region 150 of material that is attachable to the anterior frame member 70 and a posterior interface region (not shown) of material that is attachable to the posterior frame member 80. The anterior and posterior interface regions may be connected to the frame portion 20 or at least held proximate thereto via any of a number of methods. For example, a hook and loop fastener may be employed, adhesives may be used, or the interface regions may attach to the frame portion 20 at one or more discrete but distributed points of attachment. FIG. 2 illustrates an example where discrete points of attachment are employed. In this regard, for example, fixing posts 160 are provided respectively at a relatively high portion of the anterior frame member 70 and a relatively low portion of the anterior frame member 70. The anterior interface region 150 may have clips 170 that attach thereto and also attach to the fixing posts 160.

In an example embodiment, the fabric portion 30 may be attached to the posterior frame member 80 via hook and loop fasteners disposed over the interface between the posterior frame member 80 and the fabric portion, while the fabric portion 30 is attached to the anterior frame member 70 via discrete fixed locations. Moreover, in some cases, those discrete fixed locations (e.g., provided by the fixing posts 160) may be utilized in connection with a mechanism for adjusting the tightness of the fabric portion 30. As such, for example, one side of the fabric portion 30 (e.g., the front side) may be adjustably coupled to the frame portion 20, while the other side of the fabric portion 30 (e.g., the back side) may be coupled to the frame portion in a fixed or non-adjustable manner.

In some embodiments, adjustable coupling of the fabric portion 20 to the frame portion 30 (at one side or on both sides) may be accomplished using an adjustable tightening unit 180. In an example embodiment, the adjustable tightening unit 180 may be provided to enable a cord 190, string, cable or other flexible line to be threaded through a channel in a distal end of the anterior interface region 150 so that the anterior interface region 150 may be drawn toward the frame portion 20 between the clips 170 by tightening the cord 190 via the adjustable tightening unit 180. The cord 190 may be enabled to move freely throughout the channel or, in some cases, a portion of the cord 190 may be fixed at one location within the channel. The cord 190 may terminate at one of the clips 170 (e.g., the bottom clip) and extend through the anterior interface region 150 to the other clip and engage the adjustable tightening unit 180. The adjustable tightening unit 180 may, in some cases, be embodied as a cleat. Thus, for example, the cord 190 may be wrapped around a portion of the cleat at a desired tightness and then secured within the cleat. As such, the tightness of the interface between the fabric portion 30 and the frame portion 20 may be adjusted easily using one hand.

Although not required, an upper portion of the anterior frame member 70 and the posterior frame member 80 may be connected via a strap 200. The strap 200 may extend between fixing posts 160 that may be disposed on the anterior frame member 70 and the posterior frame member 80, respectively. However, any other fixing means for connection of the strap 200 may alternatively be employed. The strap 200 may perform some load bearing function, but its primary utility may be in relation to holding the frame portion 20 in a desired position or orientation. Thus, a majority of the load encountered at or exerted on the mounting plate 50 may still be borne by the fabric portion 30.

Accordingly, example embodiments may be provided to increase the comfort and the utility of a prosthetic interface by providing a structure that may be made of one to several layers of material to exhibit a graduated transition of flexible to semi-rigid or rigid materials in order to provide a comfortable platform to support a prosthetic device, but also distribute forces evenly about the body without creating pressure points. By transitioning from soft and semi-rigid materials to more rigid materials, comfort may be further enhanced where the prosthetic interface contacts the skin. The change in flexibility may be accomplished through mechanical design such as tapered laminates and through materials changes from one surface of the structure to another or other means for tapering the flexibility characteristics of materials. This may provide a gradual transition of forces from the socket system (i.e., the prosthetic interface) to the body, and may limit "edges" of the interface digging in to the soft tissue of the body.

Figure 5:
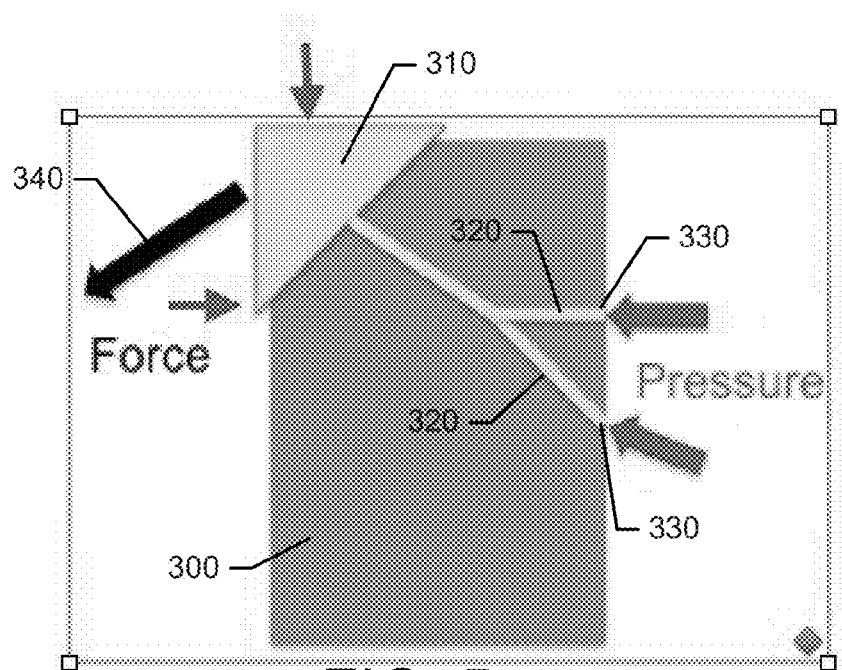
FIG. 5 illustrates an example schematic diagram of a body with a conventional prosthetic interface mounted thereon via discrete straps.
Figure 6:
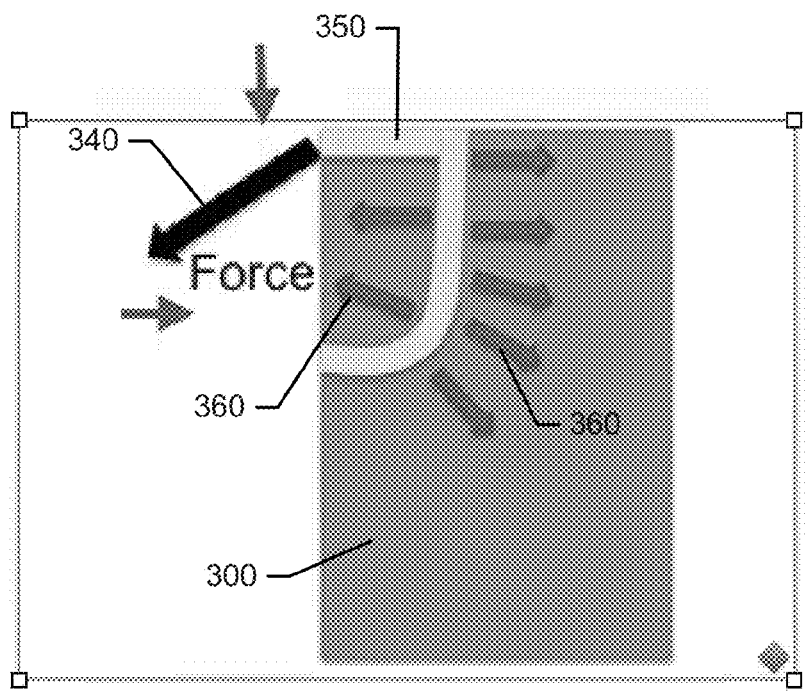
FIG. 6 illustrates a schematic diagram of a body having a prosthetic interface of an example embodiment to orients fabric components to distribute pressure evenly over the body.

FIG. 5 illustrates an example schematic diagram of a body 300 with a conventional prosthetic interface 310 mounted thereon via discrete straps 320. As can be seen from FIG. 5, the discrete straps 320 concentrate pressure at various pressure points 330 in response to loading of the interface 310 as indicated by force arrow 340. Meanwhile, by employing an example embodiment as shown in FIG. 6, the body 300 may support a prosthetic interface 350 that orients fabric components to distribute pressure evenly over the body 300. The even distribution of pressure is illustrated in FIG. 6 by virtue of the pressure arrows 360.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A prosthetic interface comprising:
   an orientation assembly comprising:
      an anterior frame portion configured to extend over an anterior portion of a torso of a wearer of the prosthetic interface, said anterior frame portion being defined by an arcuate shaped member defining an anterior frame gap, and
      a posterior frame portion configured to extend over a posterior portion of the torso, said posterior frame portion being defined by an arcuate shaped member defining a posterior frame gap,
   a mounting plate disposed at an intersection of the posterior frame portion and the anterior frame portion, the mounting plate forming a structure to which a prosthetic limb is attachable;
   a load bearing assembly comprising:
      breathable fabric forming a load distribution matrix to distribute a load on the mounting plate over portions of the torso with which the fabric is configured to be in contact, said breathable fabric being configured to extend from the anterior frame portion to the posterior frame portion around an opposite side of the torso to the side on which the mounting plate is to be worn by the wearer; and
      a drum portion made of breathable fabric and disposed to extend between the anterior frame portion proximate to the anterior frame gap and the posterior frame gap, respectively and the posterior frame portion.

2. The prosthetic interface of claim 1, wherein the drum portion distributes the load on the mounting plate away from the orientation assembly in a first direction, and wherein the fabric portion distributes the load on the mounting plate away from the orientation assembly in a second direction that is substantially opposite of the first direction.

3. The prosthetic interface of claim 1, wherein the drum portion is configured to hold one or more electrodes proximate to skin of the wearer, the electrodes being in communication with the prosthetic limb.

4. The prosthetic interface of claim 1, wherein the drum portion is attached to the anterior frame portion and the posterior frame portion via a hook and loop fastener.

5. The prosthetic interface of claim 1, wherein the fabric portion comprises material including elastane.

6. The prosthetic interface of claim 1, wherein the fabric portion is configured to extend between an arm opposite the mounting plate and the wearer's neck and between the arm and the wearer's waist.

7. The prosthetic interface of claim 1, wherein the fabric portion is affixed to the anterior frame portion or the posterior frame portion via a hook and loop fastener.

8. The prosthetic interface of claim 1, wherein the fabric portion is affixed to the posterior frame portion via a hook and loop fastener and is affixed to the anterior frame portion at one or more discrete fixed locations.

9. The prosthetic interface of claim 8, wherein coupling between the fabric portion and the one or more discrete fixed locations is adjustable.

10. The prosthetic interface of claim 9, further comprising an adjustable tightening unit configured to enable tightness of coupling between the anterior frame portion and the one or more discrete fixed locations to be adjusted.

11. The prosthetic interface of claim 10, wherein the adjustable tightening unit comprises a cleat configured to engage a cord passed through a channel disposed at an anterior interface region of the fabric portion.

12. The prosthetic interface of claim 8, wherein the one or more discrete fixed locations comprise fixing posts disposed at opposing ends of the anterior frame portion, and wherein clips are disposed at corresponding locations of the fabric portion to facilitate coupling the fabric portion to the fixing posts.

13. The prosthetic interface of claim 1, further comprising a strap configured to extend from a highest part of the anterior frame portion to a corresponding highest part of the posterior frame portion.

14. The prosthetic interface of claim 1, wherein the orientation assembly is custom fit to the wearer.

15. The prosthetic interface of claim 1, wherein the orientation assembly is a predefined size.

16. The prosthetic interface of claim 1, wherein the load bearing assembly comprises fabric straps configured to extend between two prosthetic interfaces disposed on opposite sides of the torso.

\* \* \* \* \*